(12) United States Patent
Brandom et al.

(10) Patent No.: US 8,133,959 B2
(45) Date of Patent: *Mar. 13, 2012

(54) SIDE-CHAIN CRYSTALLIZABLE POLYMERS FOR MEDICAL APPLICATIONS

(75) Inventors: Donald K Brandom, La Mesa, CA (US); Joan Zeltinger, Encinitas, CA (US); Eric V Schmid, San Diego, CA (US); Joseph J Mallon, Poway, CA (US)

(73) Assignee: REVA Medical, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/101,499

(22) Filed: May 5, 2011

(65) Prior Publication Data

US 2011/0212050 A1 Sep. 1, 2011

Related U.S. Application Data

(62) Division of application No. 11/176,638, filed on Jul. 7, 2005, now Pat. No. 7,939,611.

(60) Provisional application No. 60/586,796, filed on Jul. 8, 2004.

(51) Int. Cl.
```
C08F 28/06      (2006.01)
C08F 26/06      (2006.01)
C08F 30/02      (2006.01)
A61K 31/74      (2006.01)
A61F 2/06       (2006.01)
```
(52) U.S. Cl. ........ 526/256; 526/258; 526/274; 526/296; 424/78.08; 623/1.34

(58) Field of Classification Search .................. 526/256, 526/258, 274, 296; 424/78.08; 623/1.34
See application file for complete search history.

(56) References Cited

U.S. PATENT DOCUMENTS

| | | | |
|---|---|---|---|
| 4,638,045 A | 1/1987 | Kohn et al. | |
| 4,863,735 A | 9/1989 | Kohn et al. | |
| 4,929,494 A | 5/1990 | Matsui et al. | |
| 4,980,449 A | 12/1990 | Kohn et al. | |
| 5,163,952 A | 11/1992 | Froix | |
| 5,198,507 A | 3/1993 | Kohn et al. | |
| 5,443,477 A | 8/1995 | Marin et al. | |
| 5,466,439 A | 11/1995 | Gibby et al. | |
| 5,469,867 A | 11/1995 | Schmitt | |
| 5,670,602 A | 9/1997 | Kohn et al. | |
| 5,912,225 A | 6/1999 | Mao et al. | |
| 6,015,424 A | 1/2000 | Rosenbluth et al. | |
| 6,200,338 B1 | 3/2001 | Solomon et al. | |
| 6,238,687 B1 | 5/2001 | Mao et al. | |
| 6,375,669 B1 | 4/2002 | Rosenbluth et al. | |
| 6,388,043 B1 | 5/2002 | Langer et al. | |
| 6,475,477 B1 | 11/2002 | Kohn et al. | |
| 6,492,462 B2 | 12/2002 | Bitler et al. | |
| 6,544,453 B2 | 4/2003 | Taft et al. | |
| 6,550,480 B2 | 4/2003 | Feldman et al. | |
| 6,599,448 B1 | 7/2003 | Ehrhard et al. | |
| 6,623,521 B2 | 9/2003 | Steinke et al. | |
| 6,652,572 B2 | 11/2003 | Kugler et al. | |
| 6,831,116 B2 | 12/2004 | Bitler et al. | |
| 6,932,930 B2 | 8/2005 | DeSimone et al. | |
| 7,473,417 B2* | 1/2009 | Zeltinger et al. | 424/78.08 |
| 7,939,611 B2* | 5/2011 | Brandom et al. | 526/256 |
| 2001/0046505 A1 | 11/2001 | Kohn et al. | |
| 2004/0086458 A1 | 5/2004 | Kohn et al. | |
| 2004/0086461 A1 | 5/2004 | Kohn et al. | |
| 2004/0127970 A1 | 7/2004 | Saunders et al. | |
| 2005/0106119 A1 | 5/2005 | Brandom | |

FOREIGN PATENT DOCUMENTS

| | | |
|---|---|---|
| GB | 1 244 207 | 8/1971 |
| JP | A-62-034101 | 2/1987 |
| JP | A-07-027766 | 1/1995 |
| JP | A-07-300555 | 11/1995 |
| JP | A-10-259298 | 9/1998 |
| WO | WO 98/20928 | * 5/1998 |
| WO | WO 98/36013 | 8/1998 |
| WO | WO 98/46286 | * 10/1998 |
| WO | WO 99/24391 | * 5/1999 |
| WO | WO 2004/110313 | 12/2004 |
| WO | WO 2006/014596 | 2/2006 |
| WO | WO 2006/020616 | 2/2006 |

OTHER PUBLICATIONS

Office Action dated Apr. 15, 2010 issued in the U.S. Appl. No. 11/335,771.
Office Action dated Oct. 27, 2009 issued in the U.S. Appl. No. 11/335,771.
Aharoni, et al., "Rigid Backbone Polymers. 2. Polyisocyanates and Their Liquid-Crystal Behavior" Macromolecules, 12(1):94-103 (1979).
Andruzzi, et al., "Studies on Comb-like Polymers. 2. Poly(octadecylethylene oxide)" Macromolecules, 13:15-18(1980).
Benzina et al., "A versatile three-iodine molecular building block leading to new radiopaque polymeric biomaterials" Journal of Biomedical Materials Research, vol. 32, 459-466 (1996).
Cabasso, et al., "Radiopaque Miscible Systems Composed of Poly(Methyl Methacrylate) and Transition and Nontransition Metal Salts: Spectroscopic, Thermal, and Radiographic Characterization" Journal of Applied Polymer Science, 38:1653-1666 (1989).
Cabasso, et al., "Radiopaque Polymers Based on Acrylated Phosphonate Esters Derived from Polyols" Journal of Applied Polymer Science, 41:3025-3042(1990).
Chupov, et al., "Structure and Physico-Chemical Properties of Comb-Like Polypeptides Based on Poly-L-Lysine*" Polymer Science U.S.S.R. 21:241-252 (1979).

(Continued)

*Primary Examiner* — William Cheung
(74) *Attorney, Agent, or Firm* — Knobbe Martens Olson & Bear LLP

(57) ABSTRACT

Inherently radiopaque side-chain crystallizable polymers (IRSCCP's) are useful in various medical applications. An example of a IRSCCP is a polymer that comprises a main chain, a plurality of crystallizable side chains, and a plurality of heavy atoms attached to the polymer, the heavy atoms being present in an amount that is effective to render the polymer radiopaque. A polymeric material that includes a IRSCCP may be fabricated into a medical device useful for at least partially occluding a body cavity. For example, such a medical device may be an embolotherapy product.

23 Claims, No Drawings

OTHER PUBLICATIONS

Cretu et al., "*Synthesis and degradation of poly (2-hydroxyethyl methacrylate)-graft-poly (ε-caprolactone) copolymers*" Polymer Degradation and Stability 83 (2004) pp. 399-404.
Gonzalez, et al. "*Side-Chain Crystallinity, Heat of Melting, and Thermal Transitions in poly[N-(10-n-Alkyloxycarbonyl-n-Decyl)Maleimides] (PEMI)*" Journal of Polymer Science: Polymer Physics Edition. 18:2197-2207 (1980).
Greenberg, et al., "*Side Chain Crystallization of n-Alkyl Polymethacrylates and Polyacrylates*" Institute of Polymer Research, Polytechnic Institute of Brooklyn. 76:6280-6285. (1954).
Hutmacher et al., "*Scaffold-based tissue engineering: rationale for computer-aided design and solid free-form fabrication systems,*" TRENDS in Biotechnology vol. 22. Jul. 7, 2004, pp. 354-362.
International Search Report for Application No. PCT/US2005/024289 mailed Dec. 6, 2005.
International Search Report for Application No. PCT/US2005/028228 mailed Nov. 30, 2005.
Invitation to Pay Additional Fees in corresponding International application No. PCT/US2007/001011, mailed Mar. 4, 2008.
Jayakrishnan, et al., "Synthesis and Polymerization of Some Iodine-Containing Monomers for Biomedical Applications" Journal of Applied Polymer Science 44:743-748 (1992).
Jordan, et al., "*Side-Chain Crystallinity. I. Heats of Fusion and Melting Transitions on Selected Homopolymers Having Long Side Chains*" Journal of Polymer Science: Part A-1, 9:1835-1852 (1971).
Jordan, et al., "*Side-Chain Crystallinity. II. Heats of Fusion and Melting Transitions on Selected Copolymers Incorporating n-Octadecyl Acrylate or Vinyl Stearate*" Journal of Polymer Science:Part A-1, 9:3349-3365 (1971).
Jordan, et al., "*Side-Chain Crystallinity. III. Influence of Side-Chain Crystallinity on the Glass Transition Temperatures of Selected Copolymers Incorporating n-Octadeeyl Acrylate or Vinyl Stearate*" Journal of Polymer Science: Part A-1 9:3367-3378(1971).
Jordan, et al., "*Side-Chain Crystallinity. V. Heats of Fusion and Melting Temperatures on Monomers Whose Homopolymers Have Long Side Chains*" Journal of Polymer Science, 10:3347-3366 (1972).
Kong et al., "*Synthesis and Characterization of HEMA-PCL Macromer Grafted onto Starch*" Polymer (Korea), vol. 24. No. 2, pp. 141-148(2000).
Kruft, et al., "*In vivo tissue compatibility of two radio-opaque polymeric biomaterials*" Biomaterials, 18:31-35(1997).
Kruft, et al., "*Studies on radio-opaque polymeric biomaterials with potential applications to endovascular prostheses*" Biomaterials, 17:1803-1812 (1996).
Magagnini, et al., "*Studies on Comb-like Polymers. 1. Poly(octadecylethylene)*" Macromolecules, 13:12-15(1980).
Mao, et al. "*Synthesis and Biological Properties of Polymer Immunoadjuvants*" Polymer Journal, 25(5):499-505 (1993).
O'Driscoll, et al., "*Kinetics of Anionic Copolymerization of Monomers of Similar Polarities*" Journal of Polymer Science, 61:19-24 (1962).
Pittman, et al, "*Effect of Polymer Crystallinity on the Wetting Properties of Certain Fluroalkyl Acrylates*" Journal of Polymer Science Part A-1, 7:3053-3066 (1969).
Plate, et al., "*Comb-Like Polymers. Structure and Properties*" J. Polymer Sci.:Macromolecular Reviews, 8:117-253(1974).
Rabolt, et al., "*Studies of Chain Conformational Kinetics in Poly(di-n-alkylsilanes) by Spectroscopic Methods. 1.Poly(di-n-hexylsilane), Poly(di-n-heptylsaline), and Poly(di-n-octylsilane).*" Macromolecules, 19:611-616 (1986).
The International Search Report and the Written Opinion of the International Searching Authority in the PCT/US2007/081566. Mailing date: Aug. 28, 2008.
U.S. Appl. No. 11/200,656, filed Aug. 10, 2005.
U.S. Appl. No. 11/335,771, filed Jan. 18, 2006.
Wada, et al., "*Effect of Amount of Medium on the Radiation-Induced Polymerization of Ethylene in tert-Butyl Alcohol*" Journal of Polymer Science: Part A-1, 10:1655-1667 (1972).
Watanabe, et al., "*Thermotropic Polypeptides. 2. Molecular Packing and Thermotropic Behavior of Poly (L-glutamates) with Long n-Alkyl Side Chains*", Macromolecules 18:2141-2148 (1985).
Hooper, et al., "*Diphenolic monomers derived form the natural amino acid alpha-I-tyrosine: an evaluation of peptide coupling techniques*" Journal of Bioactive and Compatible Polymers, 10(4):327-340 XP002045571, Oct. 1995.
Overberger, et al., "*The Preparation and Polymerization of p-Alkylstyrenes. Effect of Structure on the Transition Temperatures of the Polymers*" The Department of Chemistry, Institute of Polymer Research, Polytechnic Institute of Brooklyn. 75:3326-3330, Jul. 20, 1953.
Pulapura, et al. "*Structure-Property Relationships for the Design of Polyiminocarbonates*" Biomaterials 11(9):666-678. XP000172545, Nov. 1990.

* cited by examiner

SIDE-CHAIN CRYSTALLIZABLE POLYMERS FOR MEDICAL APPLICATIONS

CROSS-REFERENCE TO RELATED APPLICATIONS

This application is a divisional application, and claims the benefit and priority of, U.S. Patent Application Ser. No. 11/176,638, filed on Jul. 7, 2005, which is now U.S. Pat. No. 7,939,611, which claims priority to U.S. Provisional Patent Application No. 60/586,796, filed Jul. 8, 2004, each of which is hereby incorporated by reference in its entirety.

BACKGROUND

1. Field of the Invention

This invention relates to side-chain crystallizable polymers, and particularly to inherently radiopaque side-chain crystallizable polymers useful in medical applications.

2. Description of the Related Art

Polymeric materials are widely used in numerous applications. For example, therapeutic embolization is the selective blockage of blood vessels or diseased vascular structures. Examples of polymeric embolotherapy devices and reagents include embolic coils, gel foams, glues, and particulate polymeric embolic agents used, for example, to control bleeding, prevent blood loss prior to or during a surgical procedure, restrict or block blood supply to tumors and vascular malformations, e.g., for uterine fibroids, tumors (i.e., chemo-embolization), hemorrhage (e.g., during trauma with bleeding) and arteriovenous malformations, fistulas (e.g., AVF's) and aneurysms.

Polymeric liquid embolic agents include precipitative and reactive systems. For example, in a precipitative system, a polymer may be dissolved in a biologically acceptable solvent that dissipates upon vascular delivery, leaving the polymer to precipitate in situ. Reactive systems include cyanoacrylate systems in which, e.g., a liquid monomeric and/or oligomeric cyanoacrylate mixture is introduced to the vascular site through a catheter and polymerized in situ. In this system, polymerization is initiated by the available water in the blood.

A number of technological applications involve the use of a polymer that undergoes a transition upon a change in temperature. For example, in the medical field, one way to introduce a solid polymer into a particular body region is to heat the polymer into a flowable state, then inject the polymer into the region and allow it to cool and solidify. U.S. Pat. No. 5,469,867 discloses side-chain crystallizable polymers that are said to be useful for occluding channels in a living mammal. Such polymers are said to be designed such that they can be melted so that they are flowable slightly above body temperature but solidify when cooled to body temperature.

SUMMARY

An embodiment provides a polymer that includes a main chain, a plurality of crystallizable side chains, and a plurality of heavy atoms attached to the polymer, the heavy atoms being present in an amount that is effective to render the polymer radiopaque. Another embodiment provides a medical device that comprises such a polymer.

Another embodiment provides a medical device that includes a polymeric material, the polymeric material comprising a biocompatible inherently radiopaque side chain crystallizable polymer.

Another embodiment provides a method of treatment that includes introducing a medical device into a body cavity of a mammal in an amount that is effective to at least partially occlude the body cavity, wherein the medical device comprises a polymeric material, and wherein the polymeric material comprises a biocompatible inherently radiopaque side chain crystallizable polymer.

Another embodiment provides a method for making an inherently radiopaque side chain crystallizable polymer, comprising copolymerizing a first monomer and a second monomer, the first monomer comprising a heavy atom and the second monomer comprising a crystallizable group.

Another embodiment provides a method for making an inherently radiopaque side chain crystallizable polymer, comprising reacting a side chain crystallizable polymer with a heavy metal reagent under conditions selected to attach a plurality of heavy atoms to the side chain crystallizable polymer.

These and other embodiments are described in greater detail below.

DETAILED DESCRIPTION OF THE PREFERRED EMBODIMENTS

An embodiment provides an inherently radiopaque side chain crystallizable polymer ("IRSCCP"). IRSCCP's may be used in a variety of applications, including medical applications in which their inherent radiopacity may provide significant advantages. The term "inherently radiopaque polymer" is used herein to refer to a polymer to which heavy atoms are attached by covalent or ionic bonds to render the polymer easier to detect by medical imaging techniques (e.g., by X-rays and/or during fluoroscopy). In this context, a "heavy atom" is an atom that, when attached to a polymer, renders the polymer easier to detect by an imaging technique as compared to a polymer that does not contain the heavy atom. Since many polymers contain relatively low atomic number atoms such as hydrogen, carbon, nitrogen, oxygen, silicon and sulfur, in most cases heavy atoms have an atomic number of 17 or greater. Preferred heavy atoms have an atomic number of 35 or greater, and include bromine, iodine, bismuth, gold, platinum tantalum, tungsten, and barium.

IRSCCP's also contain crystallizable side chains. Side chain crystallizable (SCC) polymers, sometimes called "comb-like" polymers, are well-known, see N. A. Plate and V. P. Shibaev, J. Polymer Sci.: Macromol. Rev. 8:117-253 (1974), the disclosure of which is hereby incorporated by reference. IRSCCP's may be SCC polymers that have been modified to include heavy atoms, e.g., by bonding heavy atoms to an SCC polymer and/or by making an IRSCCP by polymerizing monomers that contain heavy atoms. IRSCCP's may have various configurations, e.g., homopolymer, copolymer (e.g., random copolymer, alternating copolymer, block copolymer, graft copolymer), various tacticities (e.g., random, isotactic, atactic, syndiotactic), etc. An IRSCCP may be a mixture or blend of two or more IRSCCP's, each of the individual IRSCCP's in the mixture or blend having different configurations, molecular weights, melting points, etc. The polymer backbone or main chain of the IRSCCP, to which the crystallizable side chains are attached, may be configured in various ways, e.g., linear, branched, crosslinked, dendritic, single-stranded, double-stranded, etc. Preferred IRSCCP's for medical applications are biocompatible and/or bioresorbable. The heavy atoms may be attached to the main chain and/or the side chains of an IRSCCP.

The crystallizable side chains of IRSCCP's are preferably selected to crystallize with one another to form crystalline regions and may comprise, for example, —(CH$_2$)$_n$— and/or —((CH$_2$)$_m$—O—)$_n$ groups. The side chains are preferably linear to facilitate crystallization. For IRSCCP's that contain —(CH$_2$)$_n$— groups in the crystallizable side chain, n is preferably in the range of about 6 to about 30, more preferably in the range of about 20 to about 30. For IRSCCP's that contain —((CH$_2$)$_m$—O—)$_n$ groups in the crystallizable side chain, n is preferably in the range of about 6 to about 30 and m is preferably in the range of about 1 to about 8. More preferably, m and n are selected so that the ((CH$_2$)$_m$—O—)$_n$ groups contain from about 6 to about 30 carbon atoms, even more preferably from about 20 to about 30 carbon atoms. The spacing between side chains and the length and type of side chain are preferably selected to provide the resulting IRSCCP with a desired melting point. For example, for medical applications (e.g., embolotherapy), the spacing between side chains and the length and type of the side chains are preferably selected to provide the IRSCCP (and/or the material into which it is incorporated) with a melting point in the range of about 30° C. to about 80° C. As the spacing between side chains increases, the tendency for the side chains to be crystallizable tends to decrease. Likewise, as the flexibility of the side chains increases, the tendency for the side chains to be crystallizable tends to decrease. On the other hand, as the length of the side chains increases, the tendency for the side chains to be crystallizable tends to increase. In many cases, the length of the IRSCCP crystallizable side chain may be in the range of about two times to about ten times the average distance between crystallizable side chains.

Examples of IRSCCP's include versions of the following polymers that are modified to include sufficient heavy atoms to render them radiopaque and selected so that the alkyl group is sufficiently long (e.g., greater than about 6 carbons) to provide the desired melting point: poly(1-alkene)s, poly (alkyl acrylate)s, poly(alkyl methacrylate)s, poly(alkyl vinyl ether)s, and poly(alkyl styrene)s. Examples of IRSCCP's further include versions of the polymers disclosed in the following references that include (or have been modified to include) crystallizable side chains and sufficient heavy atoms to render them radiopaque: U.S. Pat. Nos. 4,638,045; 4,863,735; 5,198,507; 5,469,867; 5,912,225; and 6,238,687; as well as U.S. Provisional Patent Application No. 60/601,526, filed 13 Aug. 2004; all of which are incorporated by reference in their entireties, and particularly for the purpose of describing SCC polymers and methods for making them.

In an embodiment, the side chains are selected to provide the IRSCCP (or material into which the IRSCCP is incorporated) with a controllable melting temperature. In a preferred embodiment, polymeric embolotherapy products include IRSCCP's, thereby rendering the embolotherapy product detectable by a technique such as X-ray. The side chains of the included IRSCCP may be selected so that the polymeric embolotherapy product has a melting point higher than the body temperature of the mammal for which the product is intended. Such a polymeric embolotherapy product may, for example, be heated above the melting temperature to render it more flowable, thereby facilitating delivery to the target vasculature, where it may cool and solidify to embolize the vasculature. The use of IRSCCP's to provide radiopacity and a controlled melting point may be particularly advantageous in medical applications, but those skilled in the art will recognize additional applications as well. Thus, while the various descriptions herein regarding the use of IRSCCP's may indicate a preference for medical applications, it will be understood that various technologies outside the medical area may also benefit from the use of IRSCCP's.

Furthermore, in some embodiments, the present polymers may be used to develop various medical devices. For instance, pre-fabricated off-the-shelf devices, rapidly prototyped devices, real-time prototype devices using computer technology. Additionally present polymers may be delivered directly to a non-lumen or non-cavity of the body. The various medical devices may include but are not limited to stents and stent grafts for vascular and body lumen applications, pins, screws, sutures, anchors and plates for reconstructive skeletal or soft tissue applications, cartilage replacements. IRSCCP may placed directly in body tissue for example in subcutaneous and intramuscular tissue.

An embodiment of an IRSCCP is a polymer comprising a main chain, a plurality of crystallizable side chains, and a plurality of heavy atoms attached to the polymer, the heavy atoms being present in an amount that is effective to render the polymer radiopaque. A polymer that comprises a recurring unit of the formula (I) is an example of such an IRSCCP:

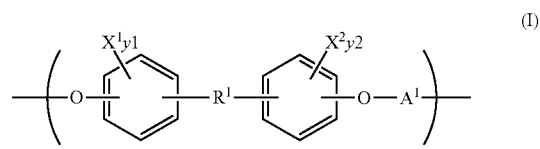

In formula (I), $X^1$ and $X^2$ are each independently selected from the group consisting of Br and I; $y^1$ and $y^2$ are each independently zero or an integer in the range of 1 to 4; and $A^1$ is selected from the group consisting of

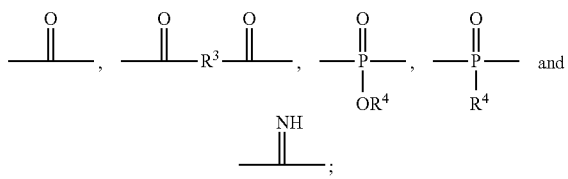

$R^3$ is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl; $R^4$ selected from the group consisting of H, $C_1$-$C_{30}$ alkyl, and $C_1$-$C_{30}$ heteroalkyl; $R^1$ is

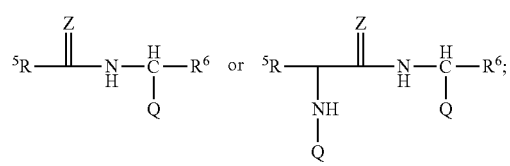

$R^5$ and $R^6$ are each independently selected from the group consisting of —CH=CH—, —CHJ$^1$-CHJ$^2$-, and —(CH$_2$)$_a$—; a is zero or an integer in the range of 1 to 8; $J^1$ and $J^2$ are each independently selected from the group consisting of Br and I; and Z is an O or an S; and Q is a crystallizable group comprising from about 6 to about 30 carbon atoms, preferably from about 20 to about 30 carbon atoms. In an embodiment, Q is:

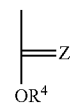

Polymers of the formula (I) may be prepared by modifying the general methods described in U.S. Provisional Patent Application No. 60/601,526, filed 13 Aug. 2004, to select the appropriate side chain length, side chain spacing and halogen content.

It will be recognized that Q and/or $R^4$ may comprise crystallizable side chains, that each of X, $J^1$ and $J^2$ is a heavy atom, and that y may be adjusted so that the number of heavy atoms in the polymer is sufficient to render the polymer radiopaque. Q and $R^4$ may each independently comprise units selected from the group consisting of —$(CH_2)_{n1}$— and —$((CH_2)_{m1}$—O—$)_{n1}$; where m1 and n1 are each independently selected so that Q and/or $R^4$ each independently contain from about 1 to about 30 carbon atoms, preferably from about 6 to about 30 carbon atoms, and more preferably from about 20 to 30 carbon atoms. Moreover, Q and $R^4$ may include other functional groups such as ester and amide, and/or heavy atoms such as iodine and bromine. Non-limiting examples of Q and $R^4$ thus include —$C_{n1}H_{2n1+1}$, —$CO_2$—$C_{n1}H_{2n1+1}$, —CONH—$C_{n1}H_{2n1+1}$, —$(CH_2)_{n1}$—Br, —$(CH_2)_{n1}$—I, —$CO_2$—$(CH_2)_{n1}$—Br, —$CO_2$—$(CH_2)_{n1}$—I, —CONH—$CO_2$—$(CH_2)_{n1}$—Br, and —CONH—$CO_2$—$(CH_2)_{n1}$—I. In an embodiment, $R^5$ is —CH=CH— or —$(CH_2)_a$—; $R^6$ is —$(CH_2)_a$—; and Q is an ester group comprising from about 10 to about 30 carbon atoms.

It will be understood that a polymer that comprises a recurring unit of the formula (I) may be a copolymer, e.g., a polymer of the formula (I) that further comprises recurring —$R^2$-$A^2$- units, where $R^2$ is selected from the group consisting of —$(CH_2)_{n2}$— and —$((CH_2)_{m2}$—O—$)_{n2}$; where m2 and n2 are each independently selected so that $R^2$ contains from about 1 to about 30 carbon atoms; and where $A^2$ is defined in the same manner as $A^1$ above. Thus, an embodiment provides a polymer comprising recurring units of the formula (Ia):

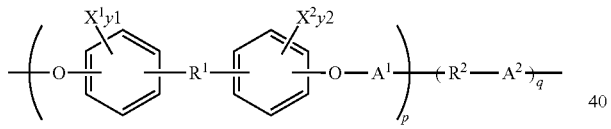

(Ia)

In formula (Ia), $X^1$, $X^2$, $y^1$, $y^2$, $R^1$ and $A^1$ are defined as described above for formula (I); p and q may each be independently varied over a broad range to provide a polymer having the desired properties, e.g., melting point, radiopacity, and viscosity, using routine experimentation. In an embodiment, p and q are each independently an integer in the range of 1 to about 10,000. It will be appreciated that the formula (I) units and —($R^2$-$A^2$)- units in a polymer comprising recurring units of the formula (Ia) may be arranged in various ways, e.g., in the form of a block copolymer, random copolymer, alternating copolymer, etc.

Another embodiment of an IRSCCP (e.g., a polymer comprising a main chain, a plurality of crystallizable side chains, and a plurality of heavy atoms attached to the polymer, the heavy atoms being present in an amount that is effective to render the polymer radiopaque) comprises a recurring unit of the formula (II):

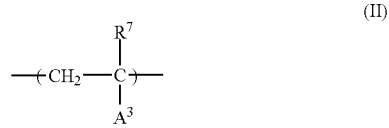

(II)

In formula (II), $R^7$ is H or $CH_3$; $A^3$ is a chemical group having a molecular weight of about 500 or less; and $A^3$ bears at least one of the heavy atoms attached to the polymer. Non-limiting examples of $A^3$ include metal carboxylate (e.g., —$CO_2Cs$), metal sulfonate (e.g., —$SO_4Ba$), halogenated alkyl ester (e.g., —$CO_2$—$(CH_2)_b$—Br), halogenated alkyl amide (e.g., —CONH—$(CH_2)_b$—Br), and halogenated aromatic (e.g., —$C_6H_4$—I), where b is an integer in the range of about 1 to about 4. In an embodiment, $A^3$ comprises an aromatic group bearing at least one halogen atom selected from the group consisting of bromine and iodine. In another embodiment, $A^3$ comprises a chemical group of the formula -$L_1$-$(CH_2)_{n3}$-$L_2$-$Ar^1$, wherein $L_1$ and $L_2$ each independently represent a nullity (i.e., are not present), ester, ether or amide group; n3 is zero or an integer in the range of about 1 to about 30; and $Ar^1$ comprises a halogenated aromatic group containing from about 2 to about 20 carbon atoms. IRSCCP's that comprise a recurring unit of the formula (II) may be formed by polymerization of the corresponding monomers or by post-reaction of appropriate polymeric precursors. IRSCCP's that comprise a recurring unit of the formula (II) may be copolymers that include additional recurring units.

Side chain $A^3$ groups in an IRSCCP comprising a recurring unit of the formula (II) may be crystallizable and/or the IRSCCP comprising a recurring unit of the formula (II) may further comprise a second recurring unit that comprises a crystallizable side chain. Examples of suitable second recurring units having crystallizable side chains include the following: poly(1-alkene)s, poly(alkyl acrylate)s, poly(alkyl methacrylate)s, poly(alkyl vinyl ether)s, and poly(alkyl styrene)s. The alkyl groups of the foregoing exemplary second recurring units preferably contain more than 6 carbon atoms, and more preferably contain from about 6 to about 30 carbon atoms. For example, in an embodiment, the second recurring unit is of the formula (III):

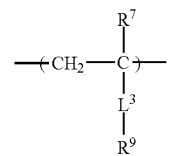

(III)

In formula (III), $R^8$ is H or $CH_3$; $L^3$ is an ester or amide linkage; and $R^9$ comprises a $C_6$ to $C_{30}$ hydrocarbon group. IRSCCP's comprising a recurring unit of the formula (II) and a second recurring unit (such as a recurring unit of the formula (III)) may be formed by copolymerization of the corresponding monomers and/or by post reaction of appropriate polymeric precursors.

Another embodiment of an IRSCCP (e.g., a polymer comprising a main chain, a plurality of crystallizable side chains, and a plurality of heavy atoms attached to the polymer, the heavy atoms being present in an amount that is effective to render the polymer radiopaque) comprises a recurring unit of the formula (IV), where $A^3$ is defined above:

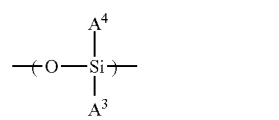

(IV)

In formula (IV), $A^4$ represents H or a group containing from about 1 to about 30 carbons, e.g., a $C_1$-$C_{30}$ hydrocarbon. Side chain $A^3$ and/or $A^4$ groups in an IRSCCP comprising a recurring unit of the formula (IV) may be crystallizable and/or the IRSCCP comprising a recurring unit of the formula (IV) may further comprise a second recurring unit that comprises a crystallizable side chain. For example, in an embodiment, the second recurring unit is of the formula (V), where $R^{10}$ comprises a $C_6$ to $C_{30}$ hydrocarbon group and $R^{11}$ represents H or a group containing from about 1 to about 30 carbons, e.g., a $C_1$-$C_{30}$ hydrocarbon:

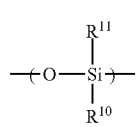

(V)

IRSCCP's are not limited to those comprising recurring units of the formulae (I) to (V), and further include versions of known polymers that have been modified to include side-chain crystallizable groups and/or sufficient heavy atoms to render the resulting polymer radiopaque. Those skilled in the art will understand that IRSCCP's may be prepared in various ways, e.g., by employing routine experimentation to modify known methods for making SCC polymers to thereby incorporate heavy atoms into the resulting polymers. For example, inherently radiopaque versions of the side chain crystallizable polymers described in U.S. Pat. No. 5,469,867 may be prepared by copolymerizing the corresponding monomers with monomers that contain heavy atoms. U.S. Pat. No. 5,469,867 is incorporated by reference and particularly for the purpose of describing monomers, polymers and methods of polymerization. Examples of suitable monomers that contain heavy atoms are disclosed in Kruft, et al., "Studies On Radio-opaque Polymeric Biomaterials With Potential Applications To Endovascular Prostheses," Biomaterials 17 (1996) 1803-1812; and Jayakrishnan et al., "Synthesis and Polymerization of Some Iodine-Containing Monomers for Biomedical Applications," J. Appl. Polm. Sci., 44 (1992) 743-748. IRSCCP's may also be prepared by post-reaction, e.g., by attaching heavy atoms to the polymers described in U.S. Pat. No. 5,469,867. Specific examples of polymers that may be modified with heavy atoms to make IRSCCP's include the acrylate, fluoroacrylate, methacrylate and vinyl ester polymers described in J. Poly. Sci, 10.3347 (1972); J. Poly. Sci. 10:1657 (1972); J. Poly. Sci. 9:3367 (1971); J. Poly. Sci. 9:3349 (1971); J. Poly. Sci. 9:1835 (1971); J.A.C.S. 76:6280 (1954); J. Poly. Sci. 7:3053 (1969); Polymer J. 17:991 (1985), corresponding acrylamides, substituted acrylamide and maleimide polymers (J. Poly. Sci.: Poly. Physics Ed. 11:2197 (1980); polyolefin polymers such as those described in J. Poly. Sci.: Macromol. Rev. 8:117-253 (1974) and Macromolecules 13:12 (1980), polyalkyl vinylethers, polyalkylethylene oxides such as those described in Macromolecules 13:15 (1980), alkylphosphazene polymers, polyamino acids such as those described in Poly. Sci. USSR 21:241, Macromolecules 18:2141, polyisocyanates such as those described in Macromolecules 12:94 (1979), polyurethanes made by reacting amine- or alcohol-containing monomers with long-chain alkyl isocyanates, polyesters and polyethers, polysiloxanes and polysilanes such as those described in Macromolecules 19:611 (1986), and p-alkylstyrene polymers such as those described in J.A.C.S. 75:3326 (1953) and J. Poly. Sci. 60:19 (1962). The foregoing polymers may be modified with heavy atoms to make IRSCCP's in various ways. For example, monomers bearing heavy atoms may be prepared by iodinating and/or brominating the monomers used to make the foregoing polymers. Those heavy atom-bearing monomers may then be copolymerized with the unmodified monomers to prepare IRSCCP's. Those skilled in the art may identify conditions for making the heavy atom-bearing monomers and corresponding IRSCCP's by routine experimentation.

In another embodiment, an IRSCCP is prepared by reacting a side chain crystallizable polymer with a heavy metal reagent under conditions selected to attach a plurality of heavy atoms to the side chain crystallizable polymer. For example, the side chain crystallizable polymer may be exposed to a heavy metal reagent that comprises bromine and/or iodine. Examples of heavy metal reagents include bromine vapor, iodine vapor, bromine solution and iodine solution. The side chain crystallizable polymer may be exposed to the heavy metal reagent by, e.g., exposing or intermixing the solid polymer with heavy metal reagent and/or by dissolving or dispersing the side chain crystallizable polymer in a solvent and intermixing with the heavy metal reagent. Other methods may also be used.

IRSCCP's may contain various amounts of heavy atoms and crystallizable side chains, depending on the properties desired for the polymer. Preferably, the content of crystallizable side chains is sufficient to substantially reduce or prevent main chain crystallization. In many cases, the amount of crystallizable side chain in the IRSCCP is in the range of about 20% to about 80% by weight, based on total polymer weight, and in some cases may be in the range of about 35% to about 65%, same basis. The length of the IRSCCP crystallizable side chain is preferably in the range of about two times to about ten times the average distance between crystallizable side chains. IRSCCP's may comprise a crystalline region (e.g., formed by crystallization of the side chains below the melting point of the polymer) and a non-crystalline region (e.g., a glassy or elastomeric region formed by the non-crystallizable portions of the IRSCCP). In an embodiment, the non-crystalline region has a glass transition temperature that is higher than the body temperature of a mammal, e.g., higher than about 37° C.; in another embodiment, the non-crystalline region has a glass transition temperature that is lower than the body temperature of a mammal, e.g., lower than about 37° C. The amount of heavy atoms in a particular IRSCCP may be selected based on the degree of radiopacity desired. For example, for medical applications, a IRSCCP preferably contains from about 1% to about 90% heavy atoms, more preferably about 20% to about 50% by heavy atoms, by weight based on total weight of IRSCCP. In some cases, the IRSCCP is incorporated into a polymeric material and/or formed into a medical device as described below. In such cases, the amount of heavy atoms in the IRSCCP may be adjusted to provide the resulting polymeric material and/or medical device with the desired degree of radiopacity.

The indiscriminate incorporation of heavy atoms into side chain crystallizable polymers often disrupts or prevents otherwise crystallizable side chains from crystallizing, particularly when the levels of heavy atom incorporation are high, the side chains are relatively short, the side chains are relatively flexible, and/or the distance between side chains is relatively large. Preferably, the heavy atoms are attached to the IRSCCP in a manner that minimizes or eliminates disruption of side chain crystallinity. For example, in an embodiment, at least about 50%, preferably at least about 80%, of the heavy atoms are attached to the main chain of the IRSCCP. In another embodiment, at least about 50%, preferably at least about 80%, of the heavy atoms are attached to the ends of the side chains of the IRSCCP, e.g., to the ends of the crystallizable side chains and/or to non-crystallizable side chains. In another embodiment, at least about 50%, preferably at least about 80%, of the heavy atoms are attached to either the main chain or the side chains (crystallizable and/or non-crystallizable) of the IRSCCP. In another embodiment, the IRSCCP is a block copolymer that comprises a crystalline block and an amorphous block, and at least about 50%, preferably at least about 80%, of the heavy atoms are attached to the amorphous block.

The molecular weight of IRSCCP's may be selected in view of the intended application for the polymer. For example, in some medical applications, e.g., for certain embolotherapy applications, it is desirable for the IRSCCP to flow at temperatures higher than the polymer melting point and to form a solid at temperatures below the polymer melting point. The viscosity of molten IRSCCP generally increases as the molecular weight of the polymer increases, and thus the molecular weight of a particular IRSCCP is preferably selected to provide the desired molten polymer viscosity. For example, a suitable molecular weight range for IRSCCP's used in embolotherapy products may be in the range of from about 2,000 to about 250,000, preferably from about 5,000 to about 150,000. Molecular weights are weight average as determined by high pressure size exclusion chromatography using light scattering detection.

In some cases, it may be desirable to mix or blend the IRSCCP with a second material (e.g., a second polymer) to form a polymeric material, which may then be employed in the intended application. For example, an embodiment provides a polymeric material that comprises a IRSCCP and a second polymer. Preferably, the second polymer is biocompatible and/or bioresorbable. Examples of second polymers suitable for mixing or blending with IRSCCP's to form polymeric materials include the non-inherently radiopaque polymers disclosed in U.S. Pat. No. 5,469,867 and the radiopaque polymers described in U.S. Provisional Patent Application No. 60/601,526, filed 13 Aug. 2004, both of which are incorporated by reference. Depending on the intended application, the relative amounts of IRSCCP and second polymer in the polymeric material may vary over a broad range. For example, in an embodiment, a polymeric material comprises from about 1% to about 100% of a IRSCCP and up to about 99% of a second polymer, by weight based on total. Since a polymeric material may consist solely of IRSCCP, it will be appreciated that the term "polymeric material" as used herein includes IRSCCP's. As noted above, it will be understood that the IRSCCP itself may be a mixture or blend of two or more individual IRSCCP's, each having, for example, different molecular weights, configurations and/or melting points.

A polymeric material that comprises a IRSCCP may be formed into various configurations or pre-formed shapes, e.g., a rod, a particle, or a sheet. A rod may be linear, coiled, hollow, highly elongated (e.g., a string or strand), and may have various cross-sections shapes, e.g., substantially round, substantially elliptical, substantially triangular, substantially rectangular, irregular, etc. A particle may be a spherical particle, a geometrically non-uniform particle (e.g., a flake or chip), a porous particle, a hollow particle, a solid particle, etc. A particle preferably has a excluded diameter of from about 10 microns to about 5,000 microns.

The configuration of the polymeric material may depend on various factors such as the intended application, shipping constraints, processing constraints, etc. For example, an embodiment provides a medical device that comprises a polymeric material. The polymeric material may comprise a IRSCCP. Various medical device embodiments are described in greater detail below. It will be appreciated that a medical device may consist solely of a polymeric material that consists solely of a IRSCCP. For example, in an embodiment, a medical device is configured to be deliverable (e.g., by injection, catheter, physical insertion, pouring, spraying and/or squirting) to a body cavity of a mammal. Such a device may be, for example, an embolotherapy product formed primarily of a polymeric material that comprises a IRSCCP. Thus, while certain descriptions below may be directed to medical devices, it will be understood that such descriptions also apply to polymeric materials and to IRSCCP's, unless the context indicates otherwise. Likewise, descriptions herein of polymeric materials and to IRSCCP's also apply to medical devices, unless the context indicates otherwise.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

Nucleating agents are materials that, in the presence of a polymer, make crystallization of the polymer more thermodynamically favorable. For example, a nucleating agent may accelerate polymer crystallization at a given temperature and/or induce crystallization (e.g., of a supercooled polymer) at a higher temperature than in the absence of the nucleating agent. Non-limiting examples of preferred nucleating agents include low molecular weight analogs of the IRSCCP's with higher peak crystallization temperatures than the bulk polymer being crystallized, carboxylate salts (such as sodium benzoate), inorganic salts (such as barium sulfate) and various particulate materials with relatively high surface area to volume ratios.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The viscosity and/or melting point of a medical device that comprises a IRSCCP typically depends on the relative amounts of the IRSCCP and other components, if any, present in the medical device. The viscosity and/or melting point of the medical device (or polymeric material in the medical device) may be controlled by manipulating the amount of IRSCCP in the medical device and by selecting a IRSCCP that provides the resulting medical device with the desired viscosity and/or melting point. Thus, for example, to provide a polymeric material that has a melting point of 40° C., it may be desirable to select a IRSCCP that has a somewhat higher melting point, e.g., about 45° C., for incorporation into the polymeric material, to compensate for the presence of a second polymer or other component that has a tendency to lower the melting point of the IRSCCP when in admixture with it. In an embodiment, a medical device comprises a polymeric material that has a melting point in the range of about 30° C. to about 80° C.

The polymeric material of the medical device is preferably configured to flow at a temperature above the melting point. The viscosity of the polymeric material at the temperature above the melting point may vary over a broad range, depending on factors such as the intended application. For example, for embolotherapy products, the polymeric material preferably has a viscosity above the melting point that allows the medical device to be delivered to the target vasculature by a convenient technique such as by injection through a syringe and/or by flowing through a catheter. In such cases, the desired viscosity often depends on the diameter of the syringe needle or catheter, e.g., lower viscosities are typically preferred at smaller diameters. On the other hand, if the viscosity is too low, the polymeric material may migrate away from the target vasculature prior to cooling and solidifying. In an embodiment, the polymeric material of the medical device has a viscosity in the range of about 50 cP to about 500 cP at the temperature above the melting point. In another embodiment, the polymeric material has a viscosity in the range of about 500 cP to about 5,000 cP at the temperature above the melting point. In another embodiment, the polymeric material has a viscosity in the range of about 5,000 cP to about 250,000 cP at the temperature above the melting point. In another embodiment, the polymeric material has a viscosity in the range of about 250,000 cP to about 1,000,000 cP at the temperature above the melting point.

In an embodiment, the polymeric material is configured to form a solid mass upon delivery to a body cavity. The solid mass may wholly or partially conform to an interior dimension of the body cavity. For example, the polymeric material may be configured to contain an amount of an IRSCCP that provides the polymeric material with a melting point of about 40° C. The polymeric material may be further configured to be deliverable to the body cavity, e.g., the polymeric material may be in the form of a rod that may be heated to a molten state to facilitate flow. The molten polymeric material may then be delivered to a body cavity by flowing through a delivery device in the molten state. Upon arrival in the body cavity, the molten polymeric material may at least partially conform to the interior dimension of the body cavity, then cool to form a solid mass. As another example, the polymeric material may be in the form of small particles suspended in a relatively low viscosity biocompatible carrier liquid such as water or saline. The polymeric material may then be caused to flow through a delivery device to the target body cavity. The small particle of polymeric material may be heated prior to delivery, during delivery and/or within the target cavity by, thereby causing the polymeric material to flow and conform to an interior dimension of the body cavity. Upon cooling, the polymeric material may form a solid mass that continues to conform to the interior dimension of the body cavity. It will be understood that polymeric materials of various configurations and formulations before heating may vary in their ability to conform to the body cavity once warmed and may therefore be selected for this reason to tailor the treatment. Further, it will be understood that the polymeric material need not be completely melted to achieve delivery. For example, a polymeric material may be formed into a particular shape, such as a coil, then implanted into the target body cavity while retaining the preformed shape. The polymeric material (e.g., coil) may be heated prior to and/or during implantation for various reasons, e.g., to render the coil more resilient and thus easier to deliver, and/or to enable the coil to better conform to the body cavity into which it is implanted. The polymeric material may also be caused to flow outside the body then be delivered to the body cavity in a flowable state.

An embodiment provides a shape memory polymeric material that comprises a IRSCCP. For example, a IRSCCP may be configured into a first shape such as a coiled shape by a standard thermoplastic formation process and crosslinked to fix the memory of the first shape. The formed IRSCCP coil may then be heated to melt the IRSCCP, allowing it to be re-configured into a second shape such as a rod shape. The cross-linking limits or prevents thermoplastic flow while the IRSCCP is in the melted state. The IRSCCP while still in the second shape may then be cooled to a temperature at which the IRSCCP recrystallizes. The recrystallization of the IRSCCP limits or prevents the second shape (e.g., the rod shape) from returning to the first shape (e.g., the coil shape). Upon re-heating to a temperature above the melting point of the IRSCCP, the second shape returns to the first shape, e.g., the rod reverts to its memory state of a coil. Crosslinking of the IRSCCP may be carried out in various ways known to those skilled in the art.

An embodiment provides a method of treatment that comprises introducing a medical device as described herein (e.g., a medical device that comprises an IRSCCP) into a body cavity of a mammal in an amount that is effective to at least partially occlude the body cavity. In general, such a method may be used to occlude any type body cavity including, e.g., various body cavities that may commonly be referred to as tubes, tubules, ducts, channels, foramens, vessels, voids, and canals. In a preferred embodiment, the medical device is an embolotherapy product. In another preferred embodiment, the body cavity comprises vasculature, e.g., an arteriovenous malformation or a blood vessel such as a varicose vein. The medical device may be introduced to the body cavity in a variety of ways, including by injection, by catheter and by surgical implantation. For a particular body cavity, the medical device is preferably selected so that the polymeric material has a melting point that is sufficiently high that the polymer forms a solid mass at the normal temperature of the body cavity, and sufficiently low so that that softened or molten polymeric material may conform to a dimension of the body cavity with little or no thermal damage to the mammal into which it is introduced. Introduction of such a polymeric material into the body cavity thus may comprise heating the polymeric material to a temperature that is higher than the melting point and/or cooling it to a temperature that is lower than the melting point.

Various types of delivery devices may be used to introduce the medical device to the body cavity, e.g., plastic tubes, catheters, fine cannula, tapered cannula and various types of syringes and hypodermic needles which are generally known to and available to those in the medical profession. An embodiment provides a medical apparatus that comprises a polymeric material and a delivery device, where the polymeric material is an IRSCCP, and where the polymeric material and the delivery device are mutually configured to facilitate delivery of the polymeric material to a body cavity by the delivery device. The polymeric material is preferably contained within the delivery device, in an amount that may vary somewhat depending on the particular body cavity to be occluded and the amount and type of occlusion desired. Those skilled in the art will be aware of the size of the cavity being occluded based on the size of the patient, general knowledge of anatomy, and thus use of diagnostic methods such as X-ray and MRI. Those skilled in the art will be able to determine the amount of polymer material to be included within the delivery device. In general, an excess amount of polymeric material should be included in the delivery device in order to provide for a certain margin of error. In an embodiment, the medical apparatus comprises an embolotherapy product and a tube, where the embolotherapy product comprises a IRSCCP as described herein and where the tube is configured to facilitate flow of the embolotherapy product to a body cavity. For example, the tube may comprise a needle, cannula, syringe, and/or catheter, and may be equipped with a heater configured to heat the embolotherapy product to a temperature above its melting point, e.g., to a temperature in the range of about 30° C. to about 80° C. The polymeric material may be included within the delivery device in a solid form or heated separately and provided in the delivery device in a flowable form. In one embodiment, the medical apparatus may be prepackaged with the polymeric material present within the delivery device and may thereafter be heated in order to make the polymeric material flowable. Heating may be applied from an exterior source such as an air, water or oil bath or an electrical heater, in which case both the delivery device and the polymeric material may be heated. Heating can also be applied from an interior source, e.g., using a small electrical resistive element at the end of a catheter through which a thin rod of the solid polymeric material is passed, or using a small laser directed at the tip of a rod of polymeric material emerging from the end of a catheter.

The delivery device may include an extrusion nozzle which is preferably relatively small in diameter such that it will not seriously damage the tissue in the vicinity of the body cavity to be occluded, but sufficiently large such that the polymeric material can be readily extruded from the nozzle. For example, in application that involves the occlusion of a body channel, the size of the nozzle is generally related to the inside diameter of the channel into which it is placed. For example, a 24 gauge needle typically fits within the opening of the punctum which leads to the canaliculus. A 2 mm catheter is typically appropriate for introducing the polymeric material into the fallopian tubes. A ¼ inch cannula is preferred for introducing the polymeric material into the inner cavity of an adult humerus. When delivered in the molten state, the polymeric material is preferably selected to have a viscosity that facilitates passage of the polymeric material through the extrusion nozzle. In general, relatively lower viscosities are preferred for relatively smaller diameter nozzles.

It will be understood that the delivery device may include an extrusion nozzle with one or more delivery ports. The polymeric material may be dispensed through multiple ports serially or simultaneously. This approach may accommodate better packing and/or stabilization of the polymeric material that cools and it may allow for delivery of more polymeric material across a large surface area. That various configurations and formulations may be simultaneously delivered by the use of various delivery ports.

For example, in an embodiment, two or more polymeric materials (each comprising a IRSCCP) may be delivered sequentially to a body cavity. In an embolotherapy embodiment, a first polymeric material is delivered to vascular structure. The first polymeric material may have a first configuration, such as a coil. The coil may be preformed, e.g., a shape memory coil as described above that is delivered in a rod shape (forming a coil upon delivery), or may be a coil that is formed during delivery by extruding the polymeric material through a delivery port of the delivery device having an appropriately configured die. The first polymeric material is preferably delivered at a temperature higher than its melting point, e.g., higher than the melting point of a first IRSCCP in the first polymeric material.

A coil may be a relatively open structure that partially occludes the vascular structure, reducing the blood flow without completely stopping it. Although such partial occlusion may be appropriate in some cases, in other cases further occlusion may be desired. Such further occlusion may be accomplished by delivering a second polymeric to the vascular structure in operable proximity to the first polymeric material. The second polymeric material is preferably delivered at a temperature higher than the its melting point, e.g., higher than the melting point of a second IRSCCP in the second polymeric material. The second polymeric material preferably has a lower viscosity than the first polymeric material, such that it may at least partially fill interstices or gaps in the first polymeric material and/or between the first polymeric material and the interior of the vascular structure. Thus, for example, the second polymeric material may have the consistency of a paste at a temperature above its melting point during delivery, allowing it to fill in the spaces of the first polymeric material coil.

One or more additional polymeric materials may be delivered to a location in operable proximity to the first and second polymeric materials. For example, the first and second polymeric materials may only partially occlude the vascular structure, although typically to a greater extend than the first polymer alone. In such a case, it may be desirable to deliver a third polymeric material to provide further occlusion. The third polymeric material is preferably delivered at a temperature higher than the its melting point, e.g., higher than the melting point of a third IRSCCP in the third polymeric material. The third polymeric material preferably has a lower viscosity than the first polymeric material, and more preferably lower than the second polymeric material, such that it may at least partially fill interstices or gaps in the polymeric mass formed by the first and second polymeric materials and/or between the mass and the interior of the vascular structure.

Those skilled in the art will appreciate that multiple variations of the embodiments described above may be practiced. For example, a single polymeric material may be delivered in multiple doses or in different forms, e.g., as a coil in a first delivery and as a paste in a second delivery, or as a paste in both the first and second deliveries. Two or more polymeric materials may be delivered simultaneously, e.g., a first polymeric material in a coil shape may be coated or mixed with a second polymeric material in a paste or liquid form to form a composite that comprises both polymers, and the resulting composite may then be delivered to the body cavity. Various body cavities may be the target of the delivery, and/or the order in which the various polymeric materials and forms are delivered may be varied. Delivery of a polymeric material that comprises a IRSCCP may be combined, sequentially or simultaneously, with the delivery of a different material, e.g., a metal embolic coil. Thus, for example, a polymeric material may be delivered to a body cavity, and a metal embolic coil may be delivered to the body cavity in contact with the polymeric material. Various periods of time may pass between deliveries, e.g., a polymeric material coil may be delivered to provide partial occlusion of a body cavity, and a second polymeric material paste may be delivered to a location in operable proximity to the coil minutes, hours, days, weeks, months, or years later.

For embodiments in which the polymeric material is delivered in the molten state, once a polymeric material has been included within the delivery device and heated to a flowable state, the nozzle of the delivery device (e.g., such as the tip of a needle, catheter, and/or squirt nozzle) may be inserted into an opening of a channel (or through the wall of cavity) to be occluded and the polymer may be dispensed out of the nozzle into the body cavity. The injection is preferably continued until the desired amount of occlusion (e.g., vasculature blockage) is obtained. In some instances, it may be desirable to occlude only part of a cavity. Thereafter, the nozzle of the delivery device may be withdrawn.

After the polymeric material has been delivered, the method may continue without operator interaction. For example, in the case of embolotherapy, the circulatory system of the mammal will typically cause a cooling effect on the surrounding tissues which will cool the injected polymeric material. The polymeric material is preferably selected such that it cools and solidifies after losing only a small amount of energy, i.e., hardens after decreasing in temperature by only a few degrees centigrade. Usually, cooling takes only a few seconds or minutes to occur, although there are times when it may be desirable for cooling to occur more slowly, e.g., in the case where a bone is reset after delivery. After cooling has taken place, the polymer preferably solidifies within the cavity in a manner conforming to the shape of the cavity and the channel is at least partially filled or blocked. The polymeric material may remain in place in the cavity over long periods of time. For preferred medical devices comprising biocompatible, non-immunogenic material, little or no adverse reaction is obtained. In certain embodiment, the polymer is bioresorbable, and thus may diminish over time, in which case surrounding tissue may fill the previously occluded region.

An effective cavity occlusion may also be achieved through the use of IRSCCP material and various excipients. For instance, the IRSCCP material may be delivered with (1) a photopolymerizable material that cross links through the use of a light; (2) a blood reactive substance that stimulates clotting such as collagen or thrombin, and/or (3) a nucleating agent.

In an embodiment, the polymeric material may be readily removed so as to again provide a cavity which functions in a normal manner. For example, it may be desirable to remove the polymeric material from a vas deferens or fallopian tube to restore fertility. The polymeric material may be removed in various ways. For example, the polymeric material may be removed by simple mechanical extraction. In certain instances, devices such as forceps and/or catheters with various attachment prongs connected thereto can be inserted into the channel and used to attach to the polymeric material and pull the polymeric material out of the cavity or force it forward into a second cavity so that the first cavity is no longer occluded and the polymeric material will not cause any damage. Alternatively, a device such as a heated wire may be brought into contact with the solidified polymeric material. By heating the polymeric material with the heated wire, the temperature of the polymeric material is raised above the melting point of the polymeric material so that it again becomes flowable. In the case of a channel (such as a duct or vein), the heating may be continued until the flowable polymeric material flows from the channel and the channel is reopened to provide normal function. In certain circumstances, the liquid plug can be drawn, aspirated or forced out of a channel, e.g., by suction with a gentle vacuum or by using mild pressure created by air or a saline flow and/or by mechanical breakup along with trapping and aspiration.

A preferred method of removing the solidified polymeric material from a channel or other cavity is to inject a lipophilic material such as a naturally occurring oil or a fatty acid ester into the channel in the area surrounding the solidified polymeric material. Preferably, a lipophilic material is selected that has a tendency to diffuse into the polymeric material, thereby reducing its melting point. The lipophilic material is preferably added in an amount that is effective to reduce the melting point of the polymeric material below body temperature to such an extent that the polymer becomes flowable. Once the polymer becomes flowable, the natural mechanical movement that occurs within channels of living beings will tend to move the polymer from the channel, thereby restoring the normal function of the channel.

EXAMPLE 1

To a resin flask equipped with a thermometer, stirrer and reflux condenser is added 500 grams (g) of octamethylcyclotetrasiloxane, 250 g of octaphenylcyclotetrasiloxane, and 250 g of octa(iodophenyl)cyclotetrasiloxane, a heavy atom-bearing monomer. The flask and contents are heated to 150° C. and 0.11 g of potassium hydroxide-isopropanol complex (neutral equivalent=193.5) is added (Si:K ratio about 4470:1). The solution is allowed to stir for approximately 30 minutes. Once the solution becomes too viscous to stir effectively (due to polymer formation), the polymer is heated to approximately 165° C. for 3 to 4 hours, then cooled to room temperature. The resulting polymer is a IRSCCP comprising recurring units of the formula (IV) in which $A^3$ and $A^4$ are iodinated phenyl groups, recurring units of the formula (V) in which $R^{10}$ and $R^{11}$ are phenyl groups, and dimethylsiloxane recurring units.

EXAMPLE 2

To a resin flask equipped with a thermometer, stirrer, reflux condenser and 250 g of xylene stirred at approximately 135° C., a solution of 20 g of 4-iodo styrene, 60 g of docosanyl acrylate, and 11 g of di-tert-butyl peroxide is added over a period of approximately 3 hours. After addition is complete, the mixture is allowed to continue stirring for approximately another 3 hours to affect a more complete conversion, then cooled to room temperature. The resulting polymer is a IRSCCP comprising recurring units of the formula (II) in which $R^7$ and $R^8$ are H, $A^3$ is $C_6H_4$—I, and recurring units of the formula (III) in which $L^3$ is an ester linkage and $R^9$ comprises a $C_{22}$ hydrocarbon group.

EXAMPLE 3

To a 500 mL 2-necked round-bottom flask equipped with a mechanical stirrer and a rubber septum, 30 g of a monomer of the formula (VI) (I2DT-docosanyl) and 240 ml of methylene chloride are added. The solids are dissolved with stirring. About 4.34 g of triphosgene dissolved in 30 mL of methylene chloride is placed in a airtight syringe and added to the reaction flask with a syringe pump at a constant rate over a period of about 2 to 3 hours. The resulting viscous polymer solution is diluted by adding about 150 mL of tetrahydrofuran and 10 mL of water. The polymer is isolated by precipitating the polymer solution in isopropanol, filtering the resulting solid and drying under vacuum. The polymer is a IRSCCP comprising a recurring unit of the formula (I) in which $X^1$ is I, $y^1$ is 2, $y^2$ is zero, $A^1$ is —(C=O)—, $R^5$ is —$CH_2CH_2$—, $R^6$ is —$CH_2$—, and Q is a crystallizable ester group containing 23 carbons.

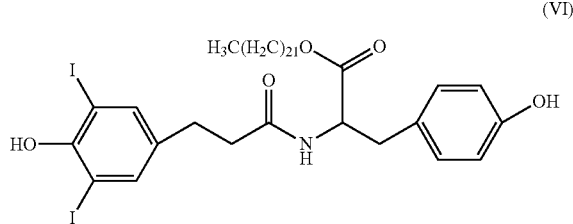

(VI)

EXAMPLE 4

An embolization is carried out as follows: A IRSCCP prepared as described in Example 3 is formed into a rod-shaped embolic medical device and loaded into a heated catheter. A physician delivers the catheter to a Arteriovenous Fistula (AVF) to be embolized. A baseline angiogram is performed with fluoroscopy to better determine the region to be embolized. The rod of IRSCCP embolic agent is pushed through the catheter to the target site. Localized heating in the catheter melts the IRSCCP, allowing it to flow through the catheter and to the target site in an liquid form that conforms to the AVF and embolizes the tissue. The IRSCCP cools and recrystallizes at the target site. Delivery of the IRSCCP is continued until blood flow ceases in the target area. Blood flow cessation is confirmed by injecting contrast agent and viewing by fluoroscopy. The IRSCCP is visible under fluoroscopy. The catheter is cooled to stop the flow of unneeded IRSCCP. The catheter is withdrawn.

EXAMPLE 5

An embolization is carried out as described in Example 4, except that a higher viscosity IRSCCP is utilized and the IRSCCP is delivered to an artery for the treatment of an aneurysm. Embolization is achieved.

EXAMPLE 6

Embolization of a traumatic bleeding artery is carried out as generally described in Example 4, except that, prior to delivery, the IRSCCP is formed into the shape of a coil and crosslinked by irradiation, thereby forming a memory coil. During heating, the memory coil softens and forms a flexible rod that is delivered to the artery through the catheter. Upon delivery, the flexible rod cools and resumes a coil shape within the artery, thereby reducing the blood flow.

It will be appreciated by those skilled in the art that various omissions, additions and modifications may be made to the materials and methods described above without departing from the scope of the invention, and all such modifications and changes are intended to fall within the scope of the invention, as defined by the appended claims.

What is claimed is:

1. A medical device that comprises a polymeric material, wherein the polymeric material comprises:
   a main chain;
   a plurality of crystallizable side chains; and
   a plurality of heavy atoms attached to the polymer, the heavy atoms being present in an amount that is effective to render the polymer inherently radiopaque.

2. The medical device of claim 1 in which the polymeric material comprises a second polymer in admixture with the inherently radiopaque polymer.

3. The medical device of claim 1 in which the inherently radiopaque polymer is bioresorbable.

4. The medical device of claim 1 that is configured to be deliverable to a body cavity of a mammal.

5. The medical device of claim 4 that is configured to be deliverable by injection or by catheter.

6. The medical device of claim 4 that comprises an embolotherapy product, the embolotherapy product comprising at least a portion of the inherently radiopaque polymer.

7. The medical device of claim 6 in which at least a portion of the inherently radiopaque polymer in the embolotherapy product is formed into at least one configuration selected from the group consisting of a rod, a particle, or a sheet.

8. The medical device of claim 4 in which the polymeric material has a melting point in the range of about 30° C. to about 80° C.

9. The medical device of claim 8 in which the polymeric material is configured to flow at a temperature above the melting point.

10. The medical device of claim 9 in which the polymeric material has a viscosity in the range of about 50 cP to about 500 cP at the temperature above the melting point.

11. The medical device of claim 9 in which the polymeric material has a viscosity in the range of about 500 cP to about 5,000 cP at the temperature above the melting point.

12. The medical device of claim 9 in which the polymeric material has a viscosity in the range of about 5,000 cP to about 250,000 cP at the temperature above the melting point.

13. The medical device of claim 9 in which the polymeric material has a viscosity in the range of about 250,000 cP to about 1,000,000 cP at the temperature above the melting point.

14. The medical device of claim 9 in which the polymeric material comprises a crystalline region and a non-crystalline region at a temperature below the body temperature of the mammal.

15. The medical device of claim 14 in which the non-crystalline region has a glass transition temperature that is higher than the body temperature.

16. The medical device of claim 14 in which the non-crystalline region has a glass transition temperature that is lower than the body temperature.

17. The medical device of claim 9 in which the polymeric material is configured to form a solid mass upon delivery to the body cavity, the solid mass at least partically conforming to an interior dimension of the body cavity.

18. The medical device of claim 17 in which the polymeric material comprises an excipient selected from the group consisting of a photopolymerizable material, a blood reactive substance and a nucleating agent.

19. The medical device of claim 17 in which the solid mass retains a preformed shape.

20. The medical device of claim 1 that further comprises an effective amount of at least one therapeutic agent.

21. The medical device of claim 20 in which the therapeutic agent is selected from the group consisting of a chemotherapeutic agent, a non-steroidal anti-inflammatory, a steroidal anti-inflammatory, and a wound healing agent.

22. The medical device of claim 1 that further comprises an effective amount of at least one magnetic resonance enhancing agent.

23. The medical device of claim 1 that is configured to be deliverable to a skeletal tissue.

* * * * *

UNITED STATES PATENT AND TRADEMARK OFFICE
CERTIFICATE OF CORRECTION

PATENT NO. : 8,133,959 B2
APPLICATION NO. : 13/101499
DATED : March 13, 2012
INVENTOR(S) : Donald K. Brandom et al.

Page 1 of 2

It is certified that error appears in the above-identified patent and that said Letters Patent is hereby corrected as shown below:

At Item 56, Page 2, Column 1, Line 33, Under Other Publications, change "n-Octadeeyl" to --n-Octadecyl--.

At Item 56, Page 2, Column 2, Line 12, Under Other Publications, change "Fluroalkyl" to --Fluoroalkyl--.

At Item 56, Page 2, Column 2, Line 31, Under Other Publications, change "form" to --from--.

At Column 4, Line 21-25, Change " 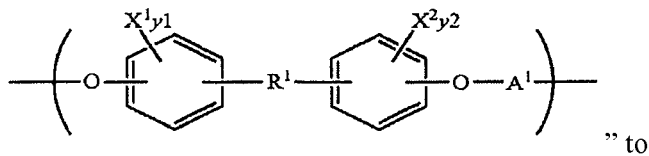 " to

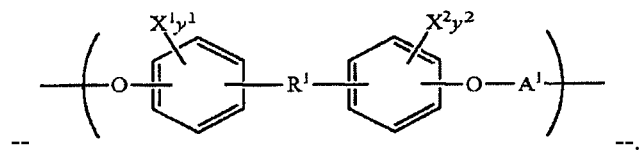
--.

At Column 4, Line 45-52, Change " 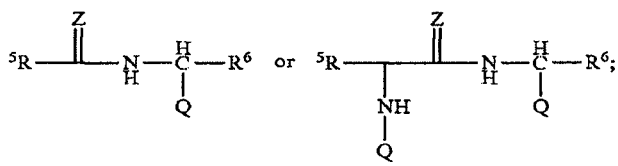 " to

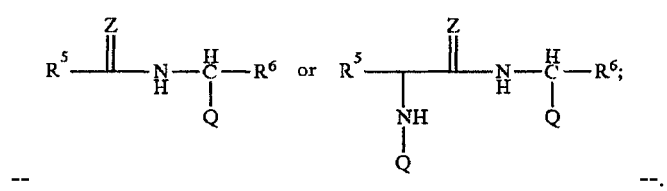
--.

Signed and Sealed this
Twenty-seventh Day of November, 2012

David J. Kappos
*Director of the United States Patent and Trademark Office*

CERTIFICATE OF CORRECTION (continued)
U.S. Pat. No. 8,133,959 B2

At Column 5, Line 36-41, Change " 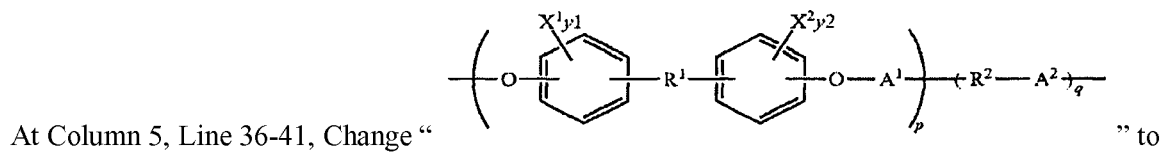 " to

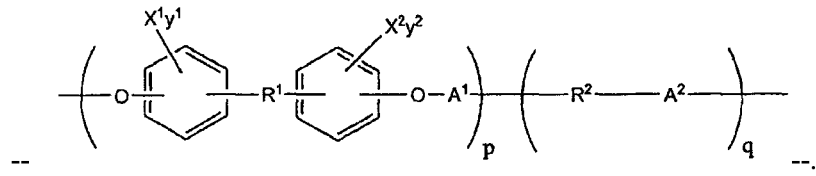

--.

At Column 5, Line 43, Change "$X^1_,$" to --$X^1$,--.

At Column 6, Line 37-44, Change " 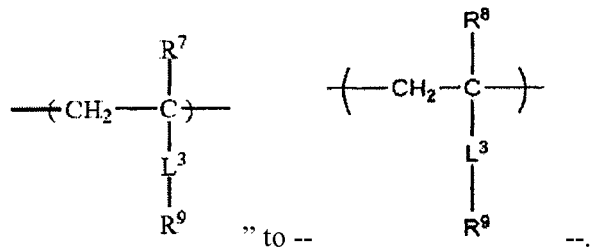 " to -- --.

At Column 7, Line 48, Change "Sci," to --Sci.--.

At Column 10, Line 32-33, Change "dioxorubicin," to --doxorubicin,--.

At Column 10, Line 36, Change "Rofexcoxib" to --Rofecoxib--.

At Column 12, Line 64, After "so that" delete "that".

At Column 14, Line 32, Change "the its" to --its--.

At Column 14, Line 51, Change "the its" to --its--.

At Column 18, Line 62, In Claim 17, change "partically" to --partially--.